(12) United States Patent
Kerboul et al.

(10) Patent No.: US 10,092,420 B2
(45) Date of Patent: Oct. 9, 2018

(54) METHOD OF ATTACHMENT OF IMPLANTABLE CUP TO A CUP IMPACTOR

(71) Applicant: Symmetry Medical Manufacturing, Inc., Warsaw, IN (US)

(72) Inventors: Guillaume Kerboul, Crudwell (GB); Stuart Weekes, Oxford (GB); James Truscott, Swindon (GB)

(73) Assignee: Symmetry Medical Manufacturing Inc., Warsaw, IN (US)

( * ) Notice: Subject to any disclaimer, the term of this patent is extended or adjusted under 35 U.S.C. 154(b) by 257 days.

(21) Appl. No.: 14/547,548

(22) Filed: Nov. 19, 2014

(65) Prior Publication Data
US 2016/0135963 A1  May 19, 2016

(51) Int. Cl.
*A61F 2/46* (2006.01)
(52) U.S. Cl.
CPC .... *A61F 2/4609* (2013.01); *A61F 2002/4627* (2013.01); *A61F 2002/4628* (2013.01); *A61F 2002/4629* (2013.01)

(58) Field of Classification Search
CPC .... A61F 2/4609; A61F 2002/4627–2002/2002
See application file for complete search history.

(56) References Cited

U.S. PATENT DOCUMENTS

| | | | |
|---|---|---|---|
| 6,626,913 B1 | 9/2003 | McKinnon et al. | |
| 7,004,946 B2* | 2/2006 | Parker | A61F 2/4609 606/99 |
| 7,037,310 B2* | 5/2006 | Murphy | A61F 2/34 606/91 |
| 7,621,921 B2* | 11/2009 | Parker | A61F 2/34 606/91 |
| 7,682,363 B2* | 3/2010 | Burgi | A61F 2/4609 606/81 |
| 7,976,548 B2 | 7/2011 | Burgi et al. | |
| 8,142,439 B2 | 3/2012 | Parker | |
| 8,236,004 B2* | 8/2012 | Jonas | A61F 2/4609 606/91 |
| 8,430,886 B2 | 4/2013 | Rushton et al. | |
| 8,585,709 B2* | 11/2013 | Burgi | A61F 2/4609 606/91 |
| 2003/0229356 A1* | 12/2003 | Dye | A61F 2/4609 606/99 |
| 2004/0153080 A1* | 8/2004 | Dong | A61B 17/1666 606/80 |
| 2009/0192515 A1* | 7/2009 | Lechot | A61F 2/4609 606/91 |
| 2010/0318192 A1* | 12/2010 | Laffay | A61F 2/34 623/22.21 |

(Continued)

*Primary Examiner* — Zade Coley
(74) *Attorney, Agent, or Firm* — Taylor IP, P.C.

(57) ABSTRACT

An orthopaedic impactor includes an elongate member having an interface end; an impact head connected to the elongate member; an implant interface held at the interface end that is configured to connect to an acetabular cup; and a securing mechanism attached to the elongate member that includes an actuator and a pressing member at least partly covering the implant interface. The pressing member is connected to the actuator and slidable relative to the implant interface. The actuator is configured to slide the pressing member along the implant interface.

3 Claims, 10 Drawing Sheets

(56) References Cited

U.S. PATENT DOCUMENTS

2013/0226186 A1* 8/2013 Burgi .................... A61B 17/56
       606/91
2014/0207200 A1* 7/2014 Kerboul ............. A61B 17/1659
       606/86 R

* cited by examiner

METHOD OF ATTACHMENT OF IMPLANTABLE CUP TO A CUP IMPACTOR

BACKGROUND OF THE INVENTION

1. Field of the Invention

The present invention relates to surgical devices, and, more particularly, to orthopaedic impactors.

2. Description of the Related Art

When performing a total hip replacement surgery, an implantable cup is required to be inserted into the acetabular cavity. The implantable cup, also referred to as an acetabular cup, is typically formed of a polymer such as polyethylene and acts as an articulating surface with the head of a femoral stem. The acetabular cup can adhere to the acetabular cavity using bone cement or by press fitting the acetabular cup into the acetabular cavity.

When a cement-less approach is used, the acetabular cup is sized to be slightly larger than the acetabular cavity and is forced into the cavity to form a tight press fit. To force the acetabular cup into the acetabular cavity, an impactor can be used. The impactor connects to the acetabular cup and has an impacting surface that a user strikes with a tool, such as a mallet, to transfer force to the connected acetabular cup and press fit the cup into the acetabular cavity. Once the acetabular cup is acceptably press fit into the acetabular cavity, the impactor is disconnected from the acetabular cup.

One possible way to connect the acetabular cup to the impactor uses corresponding threadings on the impactor and acetabular cup. The threadings are matched up and rotated so that the acetabular cup is connected to the impactor, and the reverse rotation is performed when the acetabular cup is fit in the acetabular cavity to disconnect the impactor from the acetabular cup. The threading of the impactor can be located on a rotating lever, which has a limitation on the depth of the undercut. In addition, the rotating lever uses a point contact onto the rasp undercut and has a high level of spring force.

What is needed in the art is a way to attach an acetabular cup to an impactor that can create a more secure connection between the acetabular cup and the impactor.

SUMMARY OF THE INVENTION

The present invention provides an impactor with a securing mechanism that can press into an attached acetabular cup to form a more secure connection between the acetabular cup and the impactor.

The invention in one form is directed to an orthopaedic impactor that includes an elongate member having an interface end; an impact head connected to the elongate member; an implant interface held at the interface end that is configured to connect to an acetabular cup; and a securing mechanism that is attached to the elongate member and includes an actuator and a pressing member at least partly covering the implant interface that is connected to the actuator and slidable relative to the implant surface. The actuator is configured to slide the pressing member along the implant interface.

The invention in another form is directed to a method for attaching an acetabular cup to a medical device that includes the steps of providing an orthopaedic impactor that includes an elongate member having an interface end, an impact head connected to the elongate member, an implant interface held at the interface end, and a securing mechanism attached to the elongate member that includes an actuator and a pressing member at least partly covering the implant interface that is connected to the actuator and slidable relative to the implant interface. The acetabular cup is connected to the implant interface and the pressing member is advanced against the acetabular cup using the actuator.

An advantage of the present invention is that the securing mechanism can allow for a more secure connection between the acetabular cup and the impactor.

Another advantage is that the securing mechanism can be detachable from the impactor to allow for easier cleaning.

Yet another advantage is that many different types of implant interfaces can be used to allow for connecting various acetabular cups to the impactor.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplification set out herein illustrate one embodiment of the invention and such exemplification is not to be construed as limiting the scope of the invention in any manner.

DETAILED DESCRIPTION OF THE INVENTION

Figure 1:
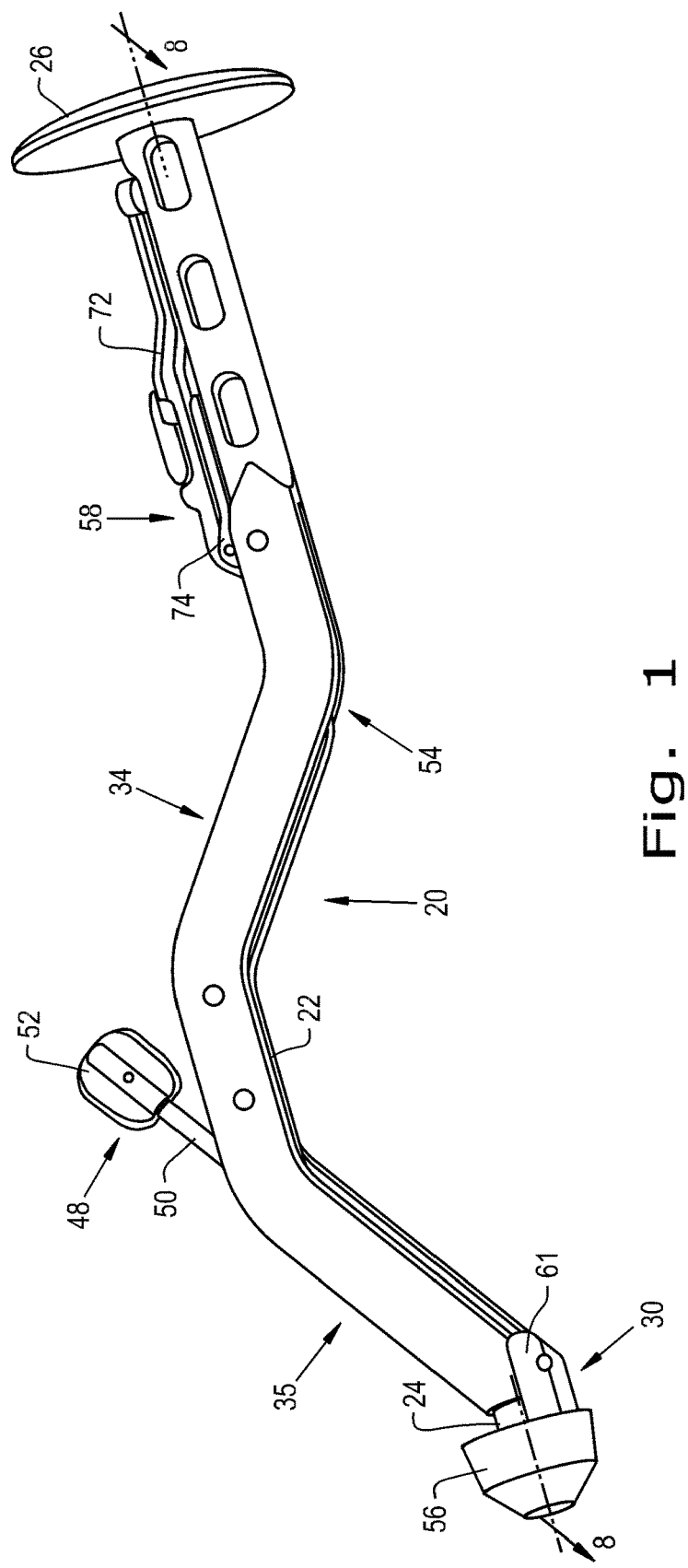
FIG. 1 is a perspective view of an orthopaedic impactor according to the present invention with a securing mechanism in a locked state.
Figure 2:
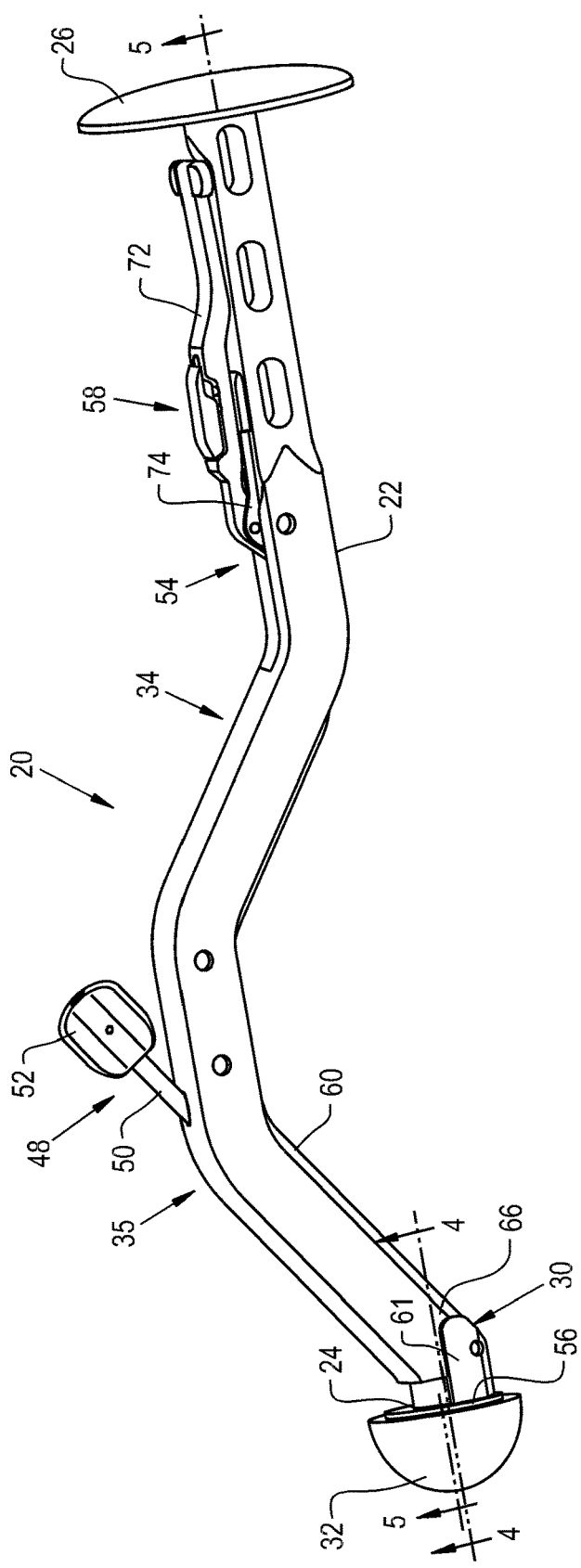
FIG. 2 is a perspective view of the orthopaedic impactor shown in FIG. 1 with an attached acetabular cup.

Referring now to the drawings, and more particularly to FIG. 1, there is shown an orthopaedic impactor 20 which generally includes an elongate member 22 that has an interface end 24, an impact head 26 connected to the elongate member 22, an implant interface 28 (shown in FIGS. 4-10) held at the interface end 24 that is configured to connect to an acetabular cup 32 (shown in FIGS. 2-7), and a securing mechanism 30 attached to the elongate member 22. As shown in FIG. 1, the orthopaedic impactor 20 is not attached to an acetabular cup. The elongate member 22 can be any suitable shape for transmitting force from the impact head 26 to the implant interface 28, which will be transferred to an attached acetabular cup. The elongate member 22 is shown as having offsets 34 and 35, but the elongate member 22 could also be a substantially straight member or have fewer or more offsets, if desired. The impact head 26 is shown as being an integral part of the elongate member 22, but this is not necessary. For example, the elongate member 22 could have a connecting point located thereon that would allow a separable impact head to be connected to the elongate member 22, which would allow for a variety of impact heads to be included on the orthopaedic impactor 20. The elongate member 22 can be formed from any material suitable to transmit force from the impact head 26 to an acetabular cup, such as metals and polymers. Since the orthopaedic impactor 20 is likely to be used in environments where contact with blood and other biological fluids or tissues will occur, it is useful if the elongate member 22 is formed from a material that is biocompatible. Such materials can include titanium, stainless steel and ultra-high molecular weight polyethylene (UHMWPE). It is also useful if the impact head 26 is formed from the same or similar materials as the elongate member 22 for the same reasons. The elongate member 22 and impact head 26 can be formed using any suitable method to produce their desired shapes, such as machining, molding, stamping, extrusion, etc.

The implant interface 28, which is shown in greater detail in FIGS. 4-10, is held at the interface end 24 of the elongate member 22 and allows the orthopaedic impactor 20 to connect to an acetabular cup 32, as shown in FIGS. 2-7. In this regard, the implant interface 28 will correspond to an interfacing feature (not numbered) included on the acetabular cup 32 to allow for the implant interface 28 to connect to the acetabular cup 32. As shown in FIGS. 4 and 6-10, the implant interface 28 can include a threading 34 that is formed on an interface tip 36. The interface tip 36 can be both threaded and unthreaded (as shown), entirely threaded, or entirely unthreaded, so long as the implant interface 28 can connect to the acetabular cup 32. The interface tip 36, as shown, includes the threading 34 at one end 38 of the interface tip 36 and has an unthreaded portion 40 at the other end 42 of the interface tip 36. The threading 34 interfaces with corresponding threading on the acetabular cup 32 to connect the acetabular cup 32 to the orthopaedic impactor 20. In this regard, the threading 34 can have a first end 44 that will not interact with the corresponding threading of the acetabular cup 32 and a second end 46 that will interface with the corresponding threading of the acetabular cup 32. The undercuts of the threading 34 and corresponding threading of the acetabular cup 32 can be altered, as desired, so long as the amount of material removed does not weaken the implant interface 28 to the point where use of the orthopaedic impactor 20 is likely to cause the implant interface 28 to fail at the threading 34. Although threading 34 is shown as being part of the implant interface 28, other interfaces could be used to detachably connect the acetabular cup 32 to the orthopaedic impactor 20 without straying from the scope of the present invention. The implant interface 28 can be formed of any material with sufficient strength to keep the orthopaedic impactor 20 connected to the acetabular cup 32 during impaction of the acetabular cup 32 into an acetabular cavity, which can include the previously described materials for forming the elongate member 22.

When the implant interface 28 includes threading 34, it is useful if the orthopaedic impactor 20 also includes a rotator 48, which can also be referred to as a cup detacher, that is rotatably connected to the implant interface 28. The rotator 48 can be an integral part of the implant interface 28 or a separable piece that is rotatably connected to the implant interface 28. As shown in the figures, the rotator 48 can include a rotational shaft 50 connected to the implant interface 28 and a rotatable knob 52 that is connected to the rotational shaft 50. The rotator 48 is held within the elongate member 22 such that it can be rotated independently of the whole orthopaedic impactor 20 by rotating the knob 52. When the rotatable knob 52 is turned, torque is transmitted through the rotational shaft 50 to the implant interface 28, which then rotates the threading 34, allowing for the threading 34 to be advanced along the corresponding threading of the acetabular cup 32 in the direction of the rotation. This rotation of the threading 34 allows for the implant interface 28 to be connected to or disconnected from the acetabular cup 32 without needing to rotate the entire orthopaedic impactor 20. When the implant interface 28 is not a threading, the cup detacher can be a different mechanism that helps detach the acetabular cup 32 from the implant interface 28.

The orthopaedic impactor 20 includes a securing mechanism 30 that is attached to the elongate member 22 and includes an actuator 54 and a pressing member 56. As can be seen, the securing mechanism 30 extends along a length of the elongate member 22 to the interface end 24, so that the pressing member 56 at least partly covers the implant interface 28. The implant interface 28 is held at the interface end 24 such that it can rotate independently of the rest of the orthopaedic impactor 20, which allows for movement of the pressing member 56 to occur independently of the implant interface 28. In this regard, the pressing member 56 can slide relative to the implant interface 28, which will be described in further detail below. The pressing member 56 can have a variety of shapes, with a useful shape being one that closely matches and corresponds to an interior surface of the acetabular cup 32, i.e., an annular shape, so that the pressing member 56 can apply a more equally distributed pressure across the interior surface of the acetabular cup 32.

As shown in FIGS. 3, 5-6 and 8-11, the actuator 54 includes a handle assembly 58 at one end and an actuating portion 60 that connects the handle assembly 58 to the pressing member 56. Movement of the handle assembly 58 relative to the elongate member 22 causes the actuating portion 60 to move relative to the elongate member 22, which causes the pressing member 56 to slide relative to the implant interface 28. This operation will be described in further detail below. While the actuator 54 is shown as including handle assembly 58 and actuating portion 60, other actuators can be used so long as they are capable of causing the pressing member 56 to slide relative to the implant interface 28. Optionally, a separate connector 61 can be connected to the elongate member 22 and link the pressing member 56 with the actuating portion 60 to cause movement of the pressing member 56 that coincides with movement of the actuating portion 60.

Figure 3:
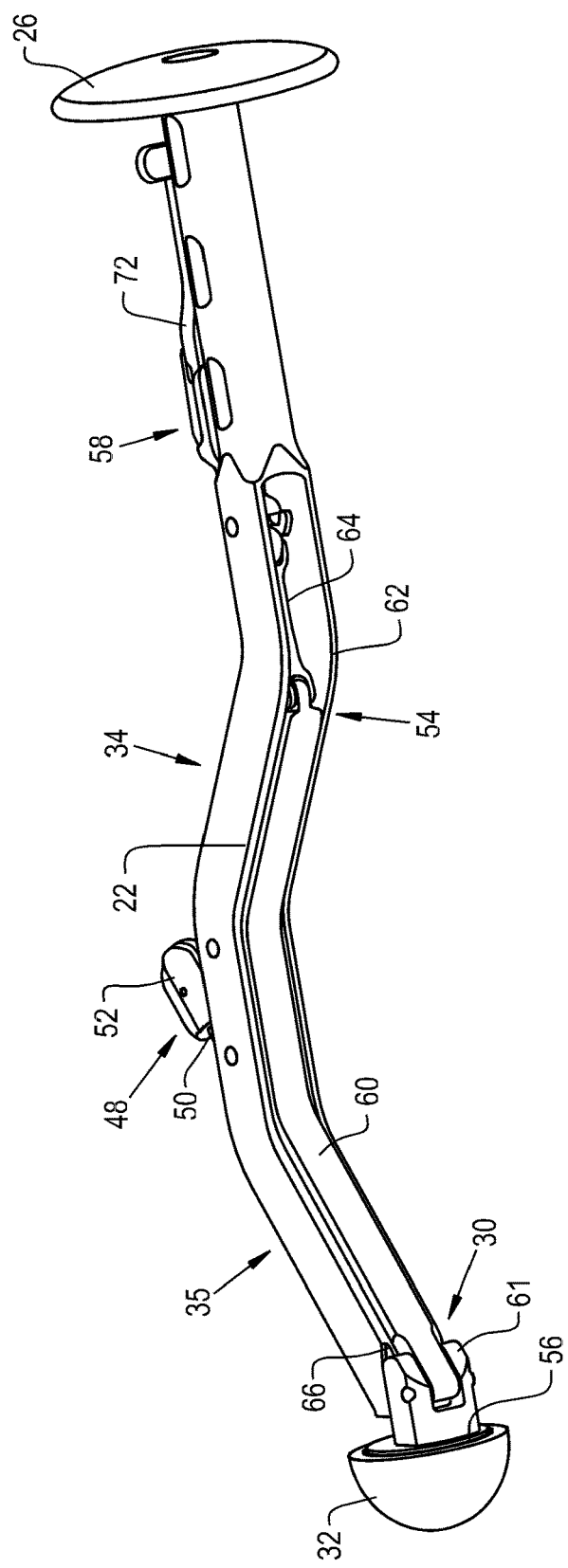
FIG. 3 is another perspective view of the orthopaedic impactor shown in FIG. 2.

Referring now to FIG. 3, it can be seen that the actuating portion 60 can be held within a slot 62 formed in the elongate member 22. Such a configuration allows for easy separability of the actuating portion 60 from the elongate member 22, if desired. It can also be seen that a linkage 64, shown as a force converting mechanism, can connect the handle assembly 58 to the actuating portion 60 to allow for movement of the handle assembly 58 to move the actuating portion 60 and connected pressing member 56. The elongate member 22 is shown as having an angled groove 66 formed adjacent to the pressing member 56, which assists in directing the motion of the connector 61 and attached pressing member 56 relative to the implant interface 28 so that the relative movement of the pressing member 56 is along the interface tip 36 of the implant interface 28.

As shown in FIG. 1, the securing mechanism 30 is in a locked state without the acetabular cup 32 connected to the implant interface 28. As can be seen, the pressing member 56 can entirely cover the interface tip 36 of the implant interface 28 in the locked state so that the threading 34 is not exposed. In this configuration, an acetabular cup cannot be attached to the implant interface 28 in the locked state, due to the threading 34 being completely covered, but it is contemplated that some of the threading 34 can be exposed in the locked state so that an acetabular cup can be connected to the implant interface 28.

Figure 4:
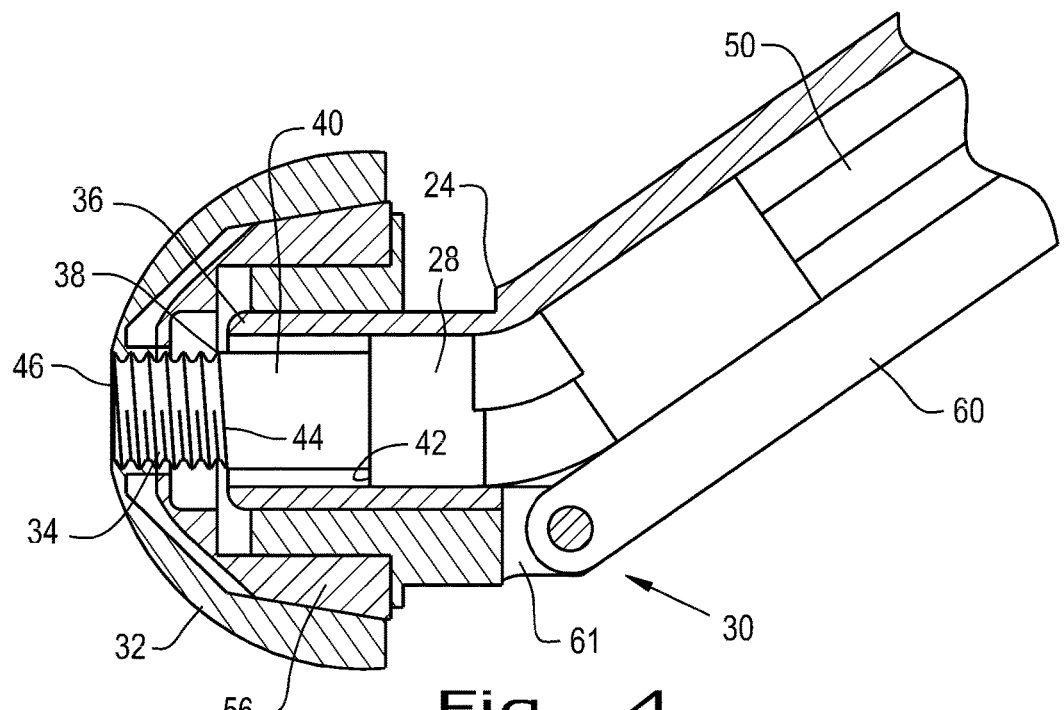
FIG. 4 is a cutaway view of the orthopaedic impactor shown in FIGS. 2-3 taken along line 4-4 with portions broken away.

When the securing mechanism 30 is in the locked state, the pressing member 56 can have a maximum extension toward the second end 46 from the first end 44 which allows the pressing member 56 to push into an acetabular cup that is connected to the implant interface 28 at the second end 46, as shown in FIG. 4. It should be appreciated that the maximum extension of the pressing member 56 is determined by how far the actuator 54 can slide the pressing member 56 along the implant interface 28 and is not necessary for the pressing member 56 to abut against the acetabular cup 32. Since the threading 34 of the interface tip 36 is mated with the corresponding threading of the acetabular cup 32 and the pressing member 56 is slidable relative to the implant interface 28 and attached acetabular cup 32, the pressing member 56 pushes on the interior surface of the acetabular cup 32 to force the corresponding threading of the acetabular cup 32 into the threading 34 of the implant interface 34. This pushing force allows for a more secure connection between the implant interface 28 and the acetabular cup 32 since slip that can occur due to threading mismatch can be corrected by the pushing force. It should be appreciated that it can be undesirable for the end of the pressing member 56 to extend past the second end 46 in the locked state, which could cause difficulties with locking the securing mechanism 30 or excessive deformation of the acetabular cup that the pressing member 56 is pushing against. While threading 34 interacting with the corresponding threading of the acetabular cup 32 is shown as the primary connection between the implant interface 28 and the acetabular cup 32, other connections could also be employed that would be more secure with the pressing member 56 pushing against an interior surface of an attached acetabular cup.

Figure 5:
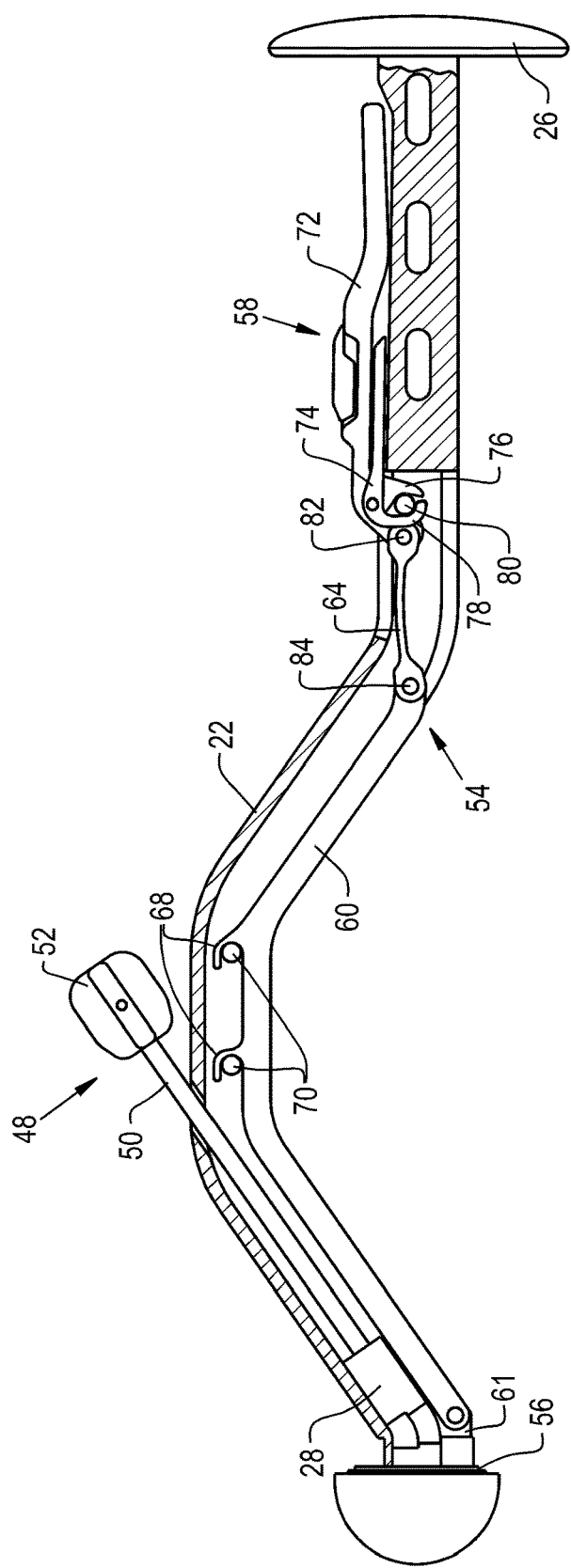
FIG. 5 is a partial cutaway view of the orthopaedic impactor shown in FIGS. 2-4 taken along line 5-5.

Referring now to FIG. 5, a cross-section of the orthopaedic impactor 20 is shown with the securing mechanism 30 in the locked state. As can be seen, the actuating portion 60 of the securing mechanism 30 includes hooks 68 that extend from the actuating portion 60 to interact with pegs 70 that are held by the elongate member 22. When the actuating portion 60 slides relative to the elongate portion 22, the hooks 68 can slide relative to the pegs 70 and grasp the pegs 70 such that further sliding of the actuating portion 60 relative to the elongate member 22 is prevented. The configuration of the hooks 68 and pegs 70 can therefore limit the maximum extension of the pressing member 56 by the actuator 54, by limiting the distance that the actuating portion 60 can slide relative to the elongate member 22.

Figure 9:
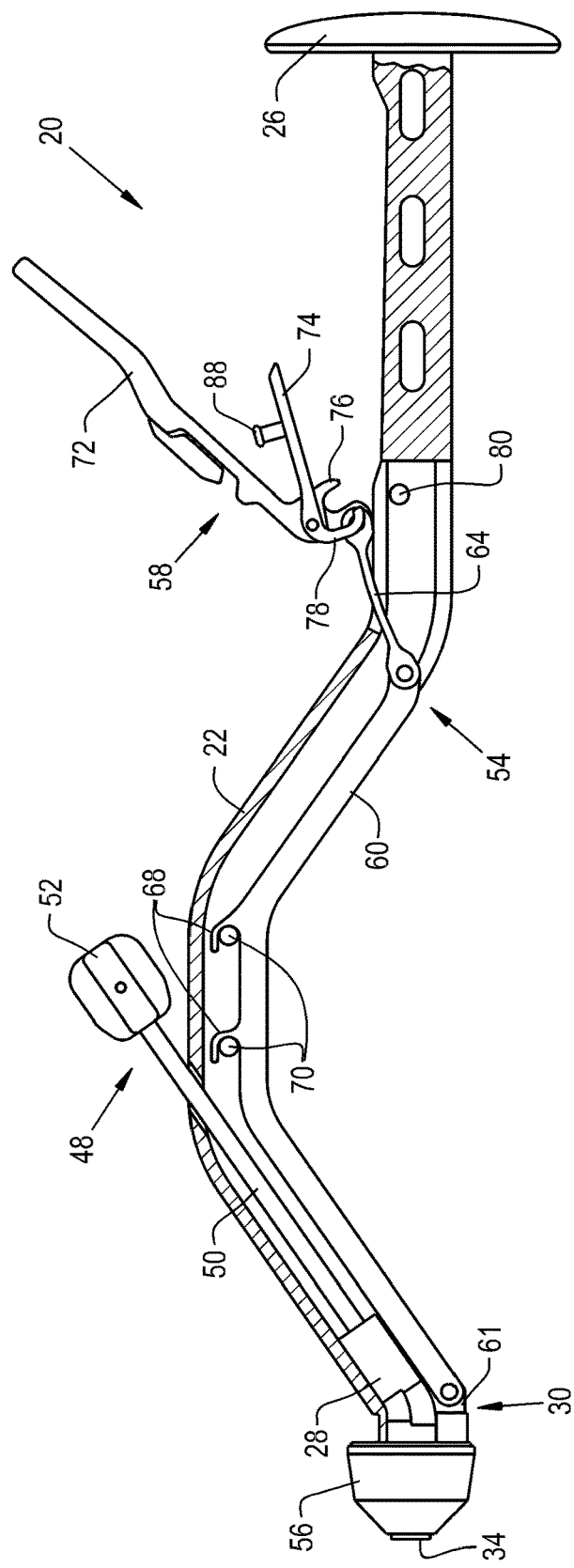
FIG. 9 is a partial cutaway view of the orthopaedic impactor shown in FIGS. 1 and 8 with a detached handle assembly.
Figure 10:
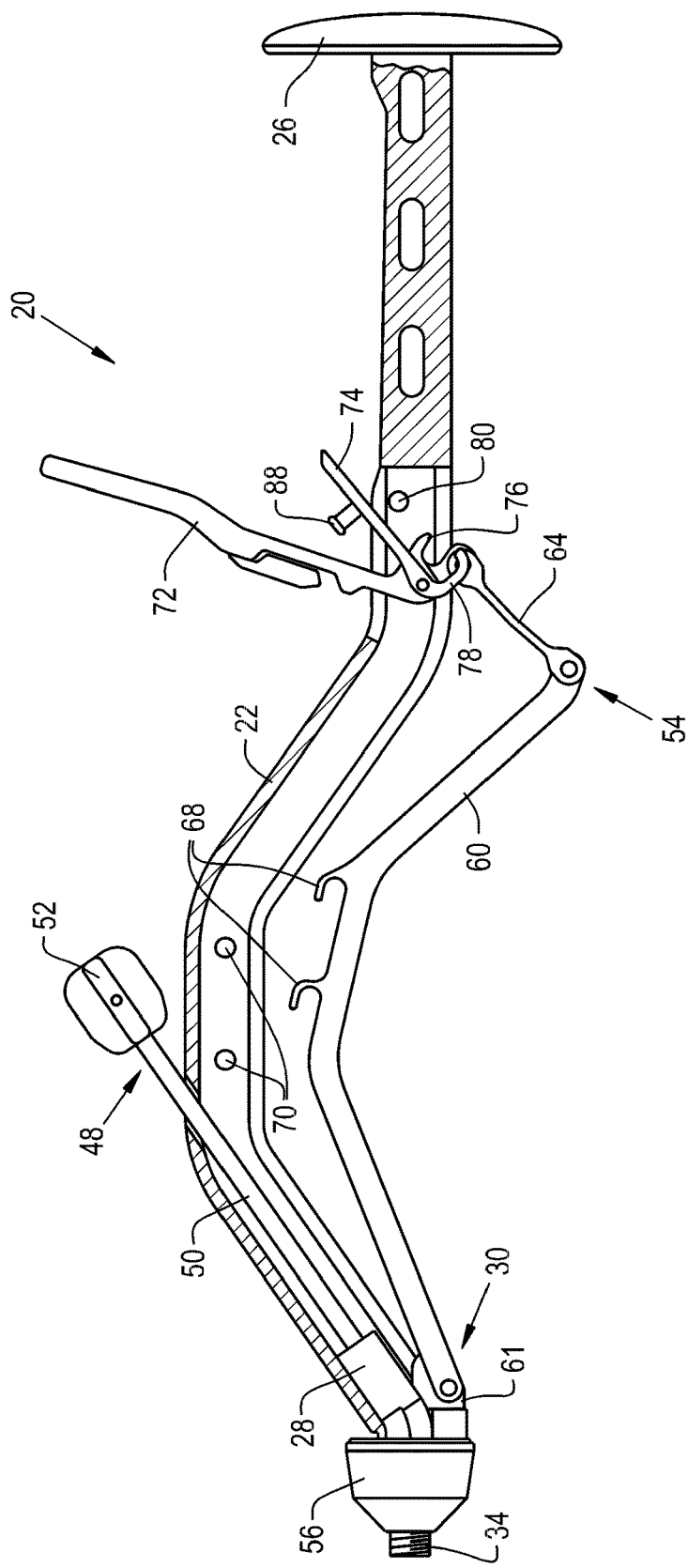
FIG. 10 is a partial cutaway view of the orthopaedic impactor shown in FIGS. 1 and 8-9 with a disengaged securing mechanism.
Figure 11:
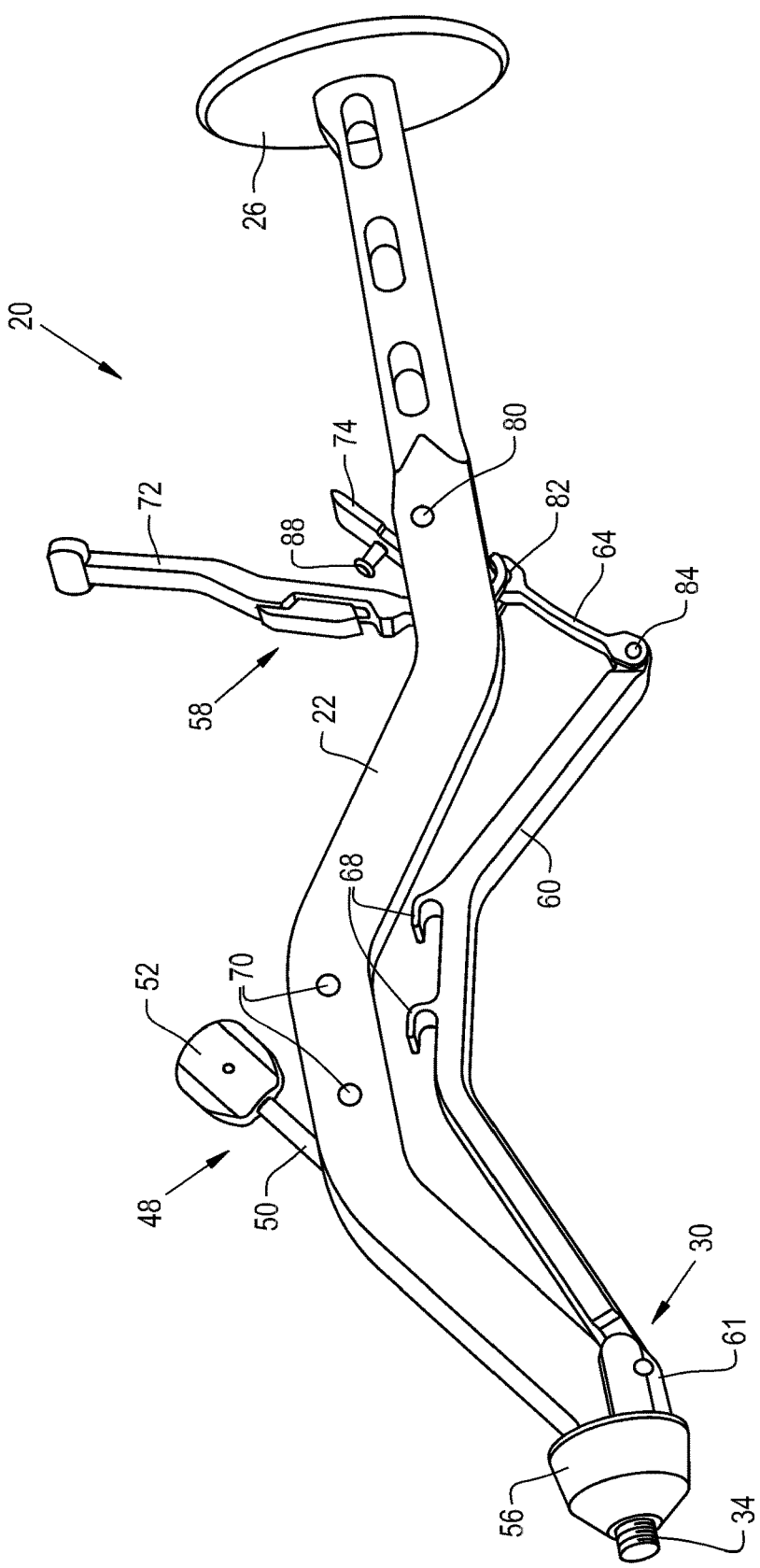
FIG. 11 is a perspective view of the orthopaedic impactor shown in FIGS. 1-10 in a disassembled state and with no attached acetabular cup.

The handle assembly 58 can include a handle portion 72 and a level latch 74 that can be connected to the handle portion 72 to form a closed handle assembly 58. The handle portion 72 and level latch 74 can each have respective grasping portions 76 and 78 with opposing shapes. This allows the grasping portions 76, 78 to come together at a pivot peg 80 that is connected to the elongate member 22, closing the grasping portions 76, 78 around pivot peg 80 to form a closed handle assembly 58 that can pivot about the pivot peg 80. The handle portion 72 and level latch 74 can be held together in a way that they are separable from one another, which is shown in FIGS. 9-11 and will be described below. While not shown, the handle assembly 58 could also grasp the pivot peg 80 without having separable pieces, if desired. As previously described, linkage 64 can connect the handle assembly 58 to the actuating portion 60. As can be seen in FIG. 5, the linkage 64 can connect to the handle portion 72 at pin 82 and to the actuating portion 60 at pin 84. The handle portion's 72 rotation about the pivot peg 80 when the handle assembly 58 is closed can move the linkage 64 in the direction of the rotation, which will move the actuating portion 60 and the pressing member 56. Therefore, the linkage 64 acts a force converting mechanism that converts rotational force moving the handle portion 72 into translational force that moves the actuating portion 60 relative to the elongate member 22.

Figure 7:
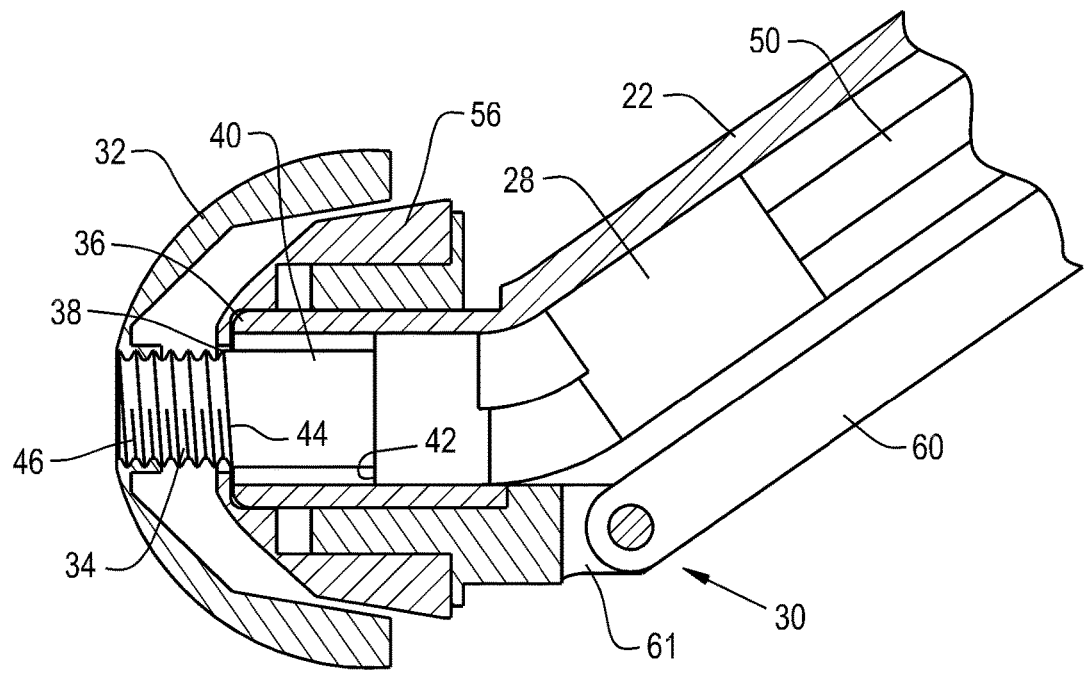
FIG. 7 is a cutaway view of the orthopaedic impactor shown in FIG. 6 with portions broken away.
Figure 6:
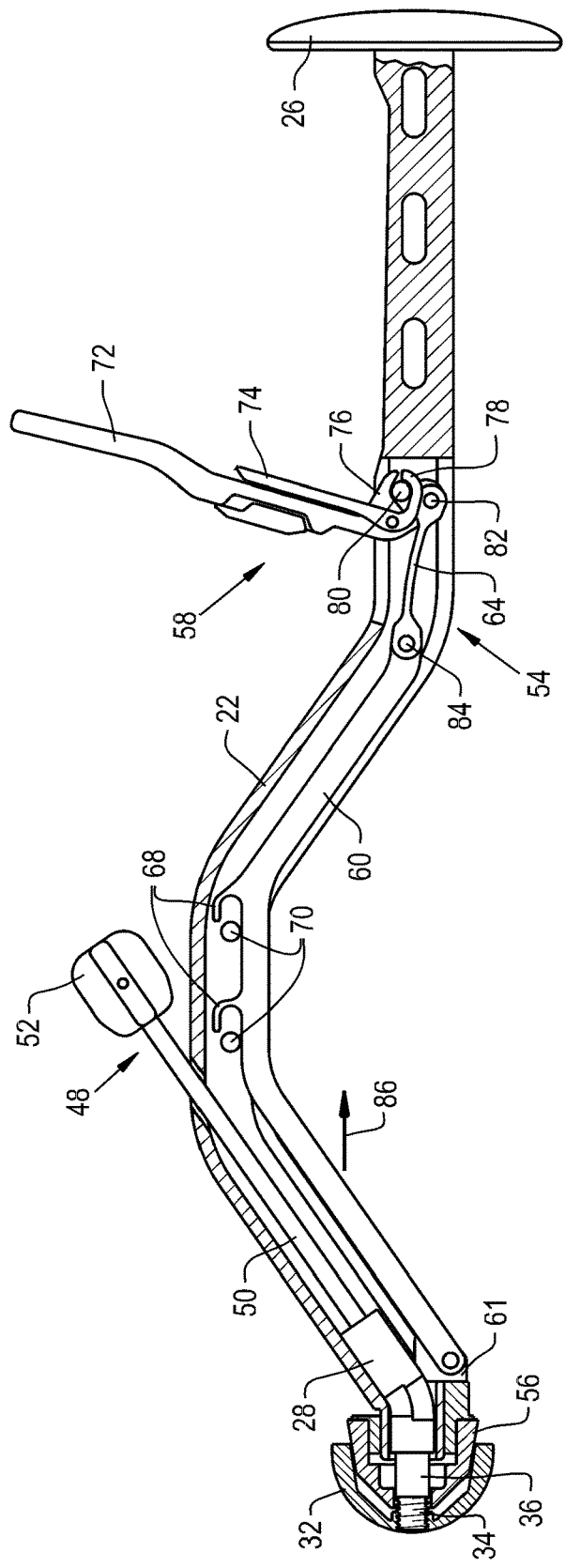
FIG. 6 is a cutaway view of the orthopaedic impactor shown in FIGS. 2-5 taken along line 4-4 in an unlocked state.
Figure 8:
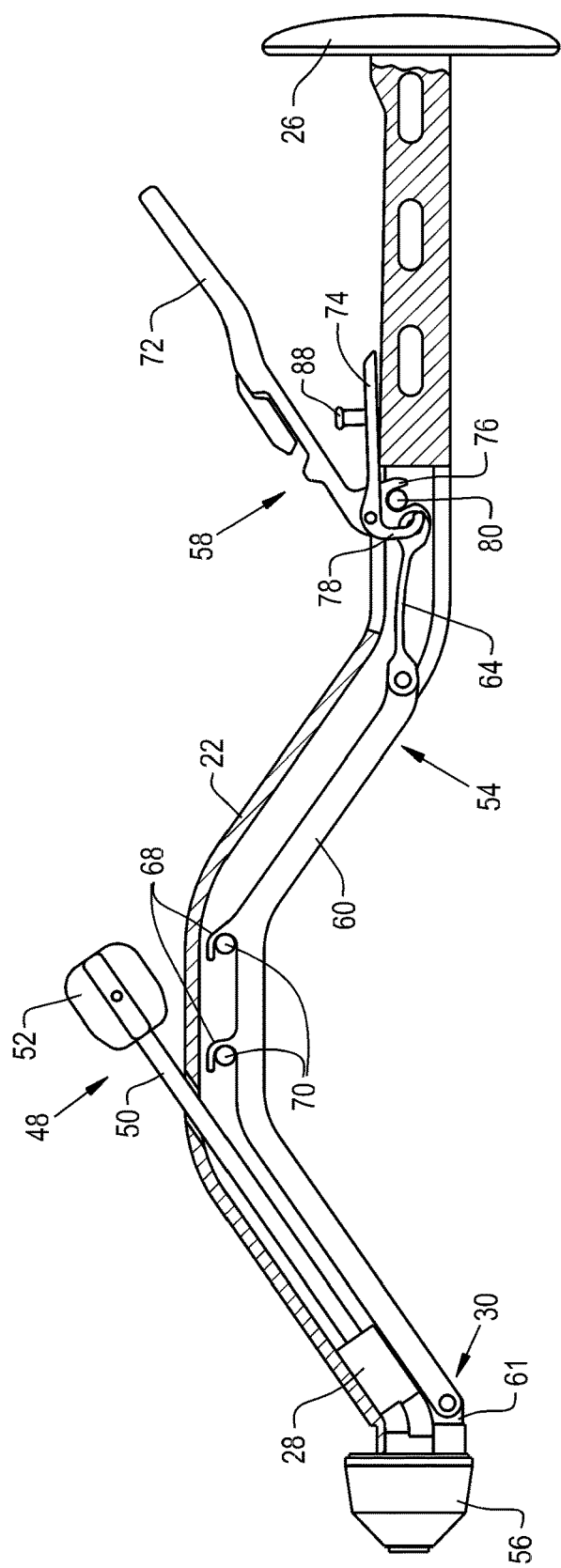
FIG. 8 is a partial cutaway view of the orthopaedic impactor shown in FIG. 1 taken along line 8-8 with an open handle assembly.

Referring now to FIGS. 6 and 7, the orthopaedic impactor 20 is shown with the securing mechanism 30 in an unlocked state, which corresponds to the closed handle assembly 58 being rotated about the pivot peg 80 away from the elongate member 22. As can be seen, the linkage 64 has been rotated with the handle assembly 58, in a direction away from the interface end 24 as indicated by an arrow 86, with the actuating portion 60 sliding in a similar direction. The sliding of the actuating portion 60 in the direction of arrow 86 therefore slides the pressing member 56 in the same direction along the implant interface 28, which takes the pressing member 56 out of contact with the interior surface of the acetabular cup 32 and can be seen in FIG. 7. In the unlocked state, the implant interface 28 does not have as secure of a connection to the attached acetabular cup 32 as in the locked state, and can be detached by twisting the rotatable knob 52 in a way that twists the threading 34 of the implant interface 28 off of the corresponding threading of the acetabular cup 32. The handle assembly 58 could also be rotated back toward the elongate member 22 to put the securing mechanism 30 back in the locked state if further impaction is necessary to seat the attached acetabular cup 32 in an acetabular cavity.

To use the orthopaedic impactor 20 shown in FIGS. 1-7, the securing mechanism 30 starts in the unlocked state to expose the threading 34 of the implant interface 28 and allow corresponding threading of the acetabular cup 32 to interact with the threading 34 to connect the acetabular cup 32 to the implant interface 28. Once the acetabular cup 32 is connected to the implant interface 28, the handle assembly 54 is rotated about the pivot peg 80 toward the elongate member 22 to put the securing mechanism 30 in the locked state, which pushes the pressing member 56 into an interior surface of the attached acetabular cup 32 and creates a more secure connection. Once the acetabular cup 32 is securely connected to the implant interface 28, a user can guide the orthopaedic impactor 20 such that the attached acetabular cup 32 is aligned with an acetabular cavity. After confirming the alignment, the user can strike the impact head 26, with the impact force being transmitted through the elongate member 22 to the acetabular cup 32 and forcing the acetabular cup 32 into the acetabular cavity. The user can continue to adjust the orthopaedic impactor 20 and strike the impact head 26 until the attached acetabular cup 32 is properly seated within the acetabular cavity. Once the acetabular cup 32 is properly seated, the user can rotate the handle assembly 58 about the pivot peg 80 away from the elongate member 22 to put the securing mechanism 30 in the unlocked state, which will move the pressing member 56 so that it no longer pushes against the acetabular cup 32. The rotatable knob 52 can then be rotated in a direction that rotates the threading 34 of the implant interface 28 off the corresponding threading of the acetabular cup 32, disconnecting the implant interface 28 from the acetabular cup 32. The orthopaedic impactor 20 can then be removed from the surgical site for cleaning.

To allow for easier cleaning of the orthopaedic impactor 20 and its components, it can be useful if the securing mechanism 30 can be separated from the elongate member 22 to increase access to the various components of the orthopaedic impactor 20. To allow for this separability, the handle assembly 58 can be detachable from the pivot peg 80, as shown in FIGS. 8-11. As can be seen, the handle portion 72 can be reversibly connected to the level latch 74 by snap fitting the handle portion 72 to a protrusion 88 formed on the level latch 74. When the handle portion 72 is snap fit to the protrusion 88, the grasping portions 76 and 78 can close around the pivot peg 80 and keep the handle assembly 58 in the closed position, as previously described. When the handle portion 72 is moved away from the level latch 74 so that it is no longer snap fit on the protrusion 88, the grasping portion 76 of the handle portion 72 separates from the grasping portion 78 of the level latch 74 so that the handle assembly 58 is in an open position and is no longer closed around the pivot peg 80, which can be seen in FIG. 8.

When the handle assembly 58 is open, the handle assembly 58 can be taken off the pivot peg 80 as shown in FIG. 9. The motion of the handle assembly 58 relative to the elongate member 22 is not constrained in the open position to just rotation, as it is in the closed position around the pivot peg 80. As such, the handle assembly 58 can be moved so that the hooks 68 of the actuating portion 60 are no longer in contact with pegs 70, as shown in FIG. 10. Removing the hooks 68 from pegs 70 frees the actuator 54 from the elongate member 22. The actuator 54 can then be separated from the pressing member 56, if separable, and removed from the elongate member 22 for cleaning or disposal, if desired. If the securing mechanism 30 is not separable into the actuator 54 and the pressing member 56, the entire securing mechanism 30 can be removed from the elongate member 22 for cleaning or disposal after unsecuring the actuator 54 and pressing member 56. Orthopaedic impactor 20 is shown in its disassembled state in FIG. 11.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic impactor, comprising:
an elongate member having an interface end;
an impact head connected to said elongate member;
an implant interface held at said interface end, said implant interface configured to connect to an acetabular cup; and
a securing mechanism attached to said elongate member including an actuator and a pressing member at least partly covering said implant interface that is connected to said actuator, an entirety of said pressing member being slidable relative to both said elongate member and said implant interface, said actuator being configured to slide said pressing member along said implant interface, wherein
said actuator includes an actuating portion connected to said pressing member and a handle assembly connected to said actuating portion, wherein movement of said handle assembly causes said pressing member to slide along said implant interface, and wherein movement of said handle assembly toward said elongate member causes movement of said actuating portion toward said impact end.

2. An orthopaedic impactor, comprising:
an elongate member having an interface end;
an impact head connected to said elongate member;
an implant interface held at said interface end, said implant interface configured to connect to an acetabular cup; and
a securing mechanism attached to said elongate member including an actuator and a pressing member at least partly covering said implant interface that is connected to said actuator, an entirety of said pressing member being slidable relative to both said elongate member and said implant interface, said actuator being configured to slide said pressing member along said implant interface, wherein
said securing mechanism has a locked state and an unlocked state, said pressing member having a maximum extension in said locked state, and wherein
said elongate member has at least one attachment peg and said actuator has at least one hook, whereby said at least one hook abuts against said at least one attachment peg in said locked state.

3. The orthopaedic impactor according to claim 2, wherein said at least one hook is separated from said at least one attachment peg in said unlocked state.

* * * * *